United States Patent [19]

Fuchs

[11] Patent Number: 4,892,624
[45] Date of Patent: Jan. 9, 1990

[54] WORKUP OF DISTILLATION RESIDUES FROM THE PURIFICATION OF CAPROLACTAM

[75] Inventor: Hugo Fuchs, Ludwigshafen, Fed. Rep. of Germany

[73] Assignee: BASF Aktiengesellschaft, Ludwigshafen, Fed. Rep. of Germany

[21] Appl. No.: 236,215

[22] Filed: Aug. 25, 1988

[30] Foreign Application Priority Data

Sep. 5, 1987 [DE] Fed. Rep. of Germany ....... 3729853

[51] Int. Cl.$^4$ .................... B01D 3/34; C07D 201/16
[52] U.S. Cl. .......................... 203/37; 203/49; 203/52; 203/69; 203/70; 203/73; 203/79; 203/85; 203/92; 203/96; 540/540
[58] Field of Search ............... 203/37, 38, 36, 52, 203/68–70, 49, 92, 93, 95–97, 79, 85, 73, 91, DIG. 25; 540/540

[56] References Cited

U.S. PATENT DOCUMENTS

| | | | |
|---|---|---|---|
| 3,037,032 | 5/1962 | Kampschmidt | 540/540 |
| 3,324,011 | 6/1967 | Baum et al. | 203/52 |
| 3,792,045 | 2/1974 | Henn et al. | 540/540 |
| 3,839,324 | 10/1974 | Schultze et al. | 540/540 |
| 4,301,073 | 11/1981 | Fuchs et al. | 540/540 |
| 4,326,925 | 4/1982 | Senni et al. | 540/540 |
| 4,582,642 | 4/1986 | Crescentini et al. | 540/540 |

FOREIGN PATENT DOCUMENTS

| | | | |
|---|---|---|---|
| 773264 | 1/1972 | Belgium | 540/540 |
| 0022161 | 11/1982 | European Pat. Off. | |
| 251553 | 11/1987 | German Democratic Rep. | 540/540 |
| 41-11332 | 6/1966 | Japan | |
| 49-4466 | 2/1974 | Japan | 540/540 |

*Primary Examiner*—Wilbur Bascomb
*Attorney, Agent, or Firm*—Keil & Weinkauf

[57] ABSTRACT

Distillation residues from the purification of caprolactam are worked up by heating in the presence of sodium hydroxide or potassium hydroxide and in the presence of a high-boiling hydrocarbon at from 250° to 500° C. and continuously removing the caprolactam.

5 Claims, No Drawings

WORKUP OF DISTILLATION RESIDUES FROM THE PURIFICATION OF CAPROLACTAM

In the course of its preparation in pure form caprolactam is separated from low-boiling and high-boiling products by distillation. The high-boiling distillation residues obtained still contain caprolactam and oligomers and polymers thereof and also non-determinable impurities and decomposition products with or without sodium hydroxide, if it was added prior to the distillation. Since these residues still contain appreciable amounts of caprolactam, it is advisable to recover it from the residue for reuse.

Japanese Patent Publication 11,332/66 discloses treating the alkaline distillation residue with fuming sulfuric acid. Owing to salt formation with the alkalis present in the residues, encrustations form in the course of distillation and give rise to problems. In another process described in EP Application 22,161, first caprolactam is distilled out of the alkaline distillation residue in a first stage at a base of column temperature of from 130° to 160° C. under reduced pressure, then in a second stage the now remaining residue is distilled at a base of column temperature of from 140° to 180° C. under reduced pressure to remove further caprolactam which is treated in a third stage with acids and recycled into the purification operation for the caprolactam from the Beckmann rearrangement. Such a process is technically complicated and still leads to residues which are difficult to handle.

It is an object of the present invention to process distillation residue from the purification of caprolactam to recover as much of the caprolactam as possible, even from the oligomers and polymers.

We have found that this object is achieved in a process for working up a distillation residue from the purification of caprolactam, which comprises heating the distillation residue in the presence of sodium hydroxide or potassium hydroxide and in the presence of a high-boiling hydrocarbon at from 250° to 500° C. and continuously removing the caprolactam from the reaction mixture.

The novel process has the advantage that caprolactam is substantially recovered from the distillation residue in a form which permits its recycling into the workup process without adverse consequences.

According to the invention, the starting point is distillation residue from the purification of caprolactam. Such distillation residue is obtained for example on separating off the caprolactam at base of column temperatures of from 120° to 150° C. under reduced pressure, for example at from 1.3 to 20 mbar. Besides caprolactam the distillation residue contains oligomers of caprolactam, polymers of caprolactam and unidentified decomposition and reaction products with or without sodium hydroxide. A suitable distillation residue is obtained for example in the process described in EP Application 22,161.

The treatment is carried out in the presence of sodium hydroxide or potassium hydroxide. It is advantageous to use from 2 to 10, in particulr from 4 to 8, parts by weight of sodium hydroxide or potassium hydroxide per part by weight of distillation residue. If the distillation residue already contains sodium hydroxide, the amount is appropriately supplemented.

In addition, the treatment of the distillation residue is carried out in the presence of a high-boiling hydrocarbon. Advantageously, the hydrocarbon used has a boiling point above 250° C., in particular from 350° to 450° C. Expediently, the boiling point of the hydrocarbon used is above that of caprolactam. Suitable hydrocarbons are high-boiling mineral oils, gas oil, vacuum gas oil, heating oil, technical grade white oil, molten paraffin wax and aromatic hydrocarbon oil. Preferably, from 0.1 to 10 parts by weight, in particular from 1 to 5 parts by weight, of high-boiling hydrocarbon are used per part by weight of distillation residue.

The treatment is carried out at from 250° to 450° C., in particular at from 280° to 380° C. In general, the treatment is carried out under atmospheric pressure or under reduced pressure, for example under from 20° to 200 mbar.

It is an essential feature of the invention that the caprolactam is removed continuously from the reaction mixture. For this purpose, it has proved advantageous to pass an inert gas through the reaction mixture. Suitable inert gases are for example nitrogen, carbon dioxide, flue gases and superheated steam. Nitrogen is particularly suitable. It is expedient to use from 1 to 100 l (S.T.P.)/hour of inert gas per kg of reaction mixture. Alternatively, it is also possible to separate off the caprolactam continuously by employing reduced pressure, as stated above, alone or by the additional use of an inert gas. The caprolactam emerging from the reaction mixture is expediently condensed by cooling or is separated off by washing with a suitable solvent, such as water. If an inert gas is used, it may expediently be recycled.

The caprolactam thus recovered is advantageously returned into the crude lactam obtained in the course of the Beckmann rearrangement after neutralization thereof. It is likewise possible to add the recovered caprolactam to the rearrangement mixture during neutralization.

The high-boiling hydrocarbon used may be used repeatedly. Expediently, the high-boiling hydrocarbon is purified, for example by filtration of centrifugation, and by washing with water or a dilute acid. If a low-cost high-boiling hydrocarbon is used, it is disposed of by undergrate firing.

The process of the invention is illustrated by the Examples below. Parts are by weight and bear the same relation to parts by volume as the kg to the l.

EXAMPLE 1

In a reaction vessel, 100 parts of a distillation residue from caprolactam production having a residual lactam content of 3% by weight and a sodium hydroxide content of 5.8% by weight are mixed with 200 parts of technical grade white oil and heated to 380° C. At the same time 10,000 parts by volume of nitrogen are passed into the mixture per hour. Caprolactam is condensed out of the emerging gases by cooling, 56.5 parts of caprolactam being obtained in the course of 1.8 hours.

EXAMPLE 2

As described in Example 1, 100 parts of a distillation residue having a residual lactam content of 3% by weight and a sodium hydroxide content of 5.8% by weight are mixed with 200 parts of technical grade white oil and heated to 330° C. The pressure is from 40 to 60 mbar, and 60 parts of caprolactam are obtained as distillate in the course of 1 hour.

I claim:

1. A process for the recovery of caprolactam from a distillation residue containing caprolactam, oligomers of caprolactam, polymers of caprolactam and unidentified decomposition and reaction products, which process comprises (a) adding to said distillation residue sodium or potassium hydroxide and per part by weight of distillation residue from 0.1 to 10 parts by weight of high boiling hydrocarbons having a boiling point above 250° C. up to 450° C., (b) heating the mixture of said distillation residue, sodium hydroxide or potassium hydroxide, and high boiling hydrocarbons to a temperature of from 250° to 450° C., and (c) removing continuously vaporized caprolactam from said heated mixture.

2. The process of claim 1 wherein a high boiling hydrocarbon having a boiling point of from 350° C. to 450° C. is used in step a.

3. The process of claim 1, wherein a temperature of from 280° to 380° C. is maintained on step b.

4. The process of claim 1, wherein reduced pressure is employed in step C.

5. The process of claim 1, wherein the vaporized caprolactam is continuously removed by passing an inert gas through the mixture of distillation residue, sodium hydroxide or potassium hydroxide, and high boiling hydrocarbons.

* * * * *